United States Patent
Nomura et al.

[11] Patent Number: 5,213,645
[45] Date of Patent: May 25, 1993

[54] METHOD FOR ATTACHMENT OF ELASTIC MEMBERS AROUND LEG-HOLES OF DISPOSABLE GARMENTS

[75] Inventors: Hironori Nomura, Iyomishima; Taiji Shimakawa, Kanonji; Yoshinori Matsura; Hiroki Yamamoto, both of Kagawa; Hirofumi Ohnishi, Iyomishima, all of Japan

[73] Assignee: Uni-Charm Corporation, Ehime, Japan

[21] Appl. No.: 871,687

[22] Filed: Apr. 21, 1992

[30] Foreign Application Priority Data

Apr. 25, 1991 [JP] Japan ................... 3-122429

[51] Int. Cl.⁵ ............... B32B ⁿ˙/10; A61F 13/15
[52] U.S. Cl. .................... 156/164; 156/229; 156/204; 156/265; 156/301; 156/494
[58] Field of Search ........... 156/164, 265, 301, 299, 156/161, 229, 204, 494, 495, 269, 267, 519, 302; 604/385.2

[56] References Cited

U.S. PATENT DOCUMENTS

| | | | |
|---|---|---|---|
| 4,364,787 | 12/1982 | Radzins | 156/164 |
| 4,413,623 | 11/1983 | Dieniak | 156/229 X |
| 4,488,923 | 12/1984 | Dieniak | 156/229 X |
| 4,650,530 | 3/1987 | Mahoney et al. | 156/204 X |
| 5,055,103 | 10/1991 | Nomura et al. | 604/385.2 |
| 5,080,741 | 1/1992 | Nomura et al. | 156/226 X |
| 5,147,487 | 9/1992 | Nomura et al. | 156/161 X |

FOREIGN PATENT DOCUMENTS

| | | |
|---|---|---|
| 0048011 | 3/1982 | European Pat. Off. . |
| 0405575 | 2/1991 | European Pat. Off. . |
| 0417766 | 3/1991 | European Pat. Off. . |
| 2196834 | 5/1988 | United Kingdom . |
| 2234157 | 1/1991 | United Kingdom . |

Primary Examiner—Jeff H. Aftergut
Attorney, Agent, or Firm—Fred Philpitt

[57] ABSTRACT

Here is disclosed a method for efficiently attaching elastic members around leg-holes of a garment such as a disposable diaper or the like without any futile use of material.

Elastic members 04A, 04B are fed and bonded onto a web so that the respective elastic members described curves like sine curves with summits and troughs of these curves defining together respective annular elastic areas 16 and thereby a base web is formed. Then the base web is severed into strips 17' bearing thereon the individual annular elastic areas and these strips 17' are intermittently bonded to a web 07 to form a composite web 19. A separate web is bonded onto a top surface of the composite web 19 to form a composite web 20. Finally, the composite web 20 is severed along center lines of the respective annular elastic areas 16 into individual garments.

4 Claims, 7 Drawing Sheets

METHOD FOR ATTACHMENT OF ELASTIC MEMBERS AROUND LEG-HOLES OF DISPOSABLE GARMENTS

BACKGROUND OF THE INVENTION

This invention relates to a method for attachment of elastic members around leg-holes of disposable garments such as diapers, training pants or incontinence pants.

There have already been proposed various methods for attachment of elastic members around leg-holes of disposable garments and some of them have been put to practical use. The inventors also disclosed, in EP 0405575, a method suitable for attachment of elastic members around leg-holes of disposable garments such as training pants with the elastic members being curved so that the garments may well fit the wearer's legs.

However, the garments made by such method of prior art has a problem that a useless portion of the elastic members is left between both leg-holes. Specifically, when nonwoven fabric or plastic film being rather translucent is used as material for top- and backsheets of the garments, the useless portion of the elastic members will be apt to be seen through these sheets, not only making the garments unattractive but also increasing the manufacturing cost since the elastic members used in each garment is increased by an amount corresponding to the useless portion. While it is possible, during a process of manufacturing, to sever the useless portion of the elastic members, it remains unchanged that the amount of material corresponding to the useless portion is additionally necessary.

Accordingly, it is an object of the invention to provide a method for attachment of the elastic members around the leg-holes of disposable garments, which basically employ the method of prior art but is free from the above-mentioned problems accompanying this well known method.

It is another object of the invention to provide a method for attachment of the elastic members around the leg-holes of disposable garments, by which a stretch stress of the elastic member for each leg-hole is distributed substantially on upper half of this leg-hole.

SUMMARY OF THE INVENTION

The objects set forth above are achieved, in accordance with the invention, a method, which is applicable to the garments of both waist-hole open type and waist-hole closed type, basically comprising the following steps of:

forming a base web by continuously feeding and bonding with adhesive first and second continuous elastic members, while keeping them stretched, onto a top surface of a first web, which is being moved, so that the elastic members discribe curves like sine curves, with summits as well as troughs of the respective curves being symmetrically opposed to each other, and cross each other at their ends so as to form annular elastic areas; forming a first composite web by severing the base web along respective lines transversely extending through respective crossings at which the first and second continuous elastic members cross each other and intermittently bonding respective severed strips with adhesive onto second web, which is being moved, along its longitudinally extending central area; forming a second composite web by bonding a third web being moved with adhesive onto a top surface of the first composite web; forming continuous garments by cutting off portions of the second composite web surrounded by the respective annular elastic areas to form notches for the leg-holes; and obtaining individual garments by severing the continuous garments along lines each dividing the associated one of the annular elastic areas in two longitudinally of the second composite web.

For the garments of waist-hole closed type, the continuous garments are formed by transversely folding the second composite web in two along its longitudinally extending central line, then providing the folded second composite web with transverse seal lines along the lines dividing the respective annular elastic areas in two and thereby defining the individual garments. These individual garments are severed off from the continuous garments so as to leave the seal lines and thereby to define side edges of the respective individual garments.

Normally, the second web comprises a liquid-permeable sheet and the third web comprises a liquid-impermeable sheet. To obtain the garments having the liquid absorbent core, each absorbent core is located between each pair of adjacent the annular elastic areas on the first composite web before the third web is laid on the first composite web.

These and other features and advantages of the invention will be better understood from the following description made in reference with the accompanying drawings.

PREFERRED EMBODIMENTS OF THE INVENTION

Figure 1:
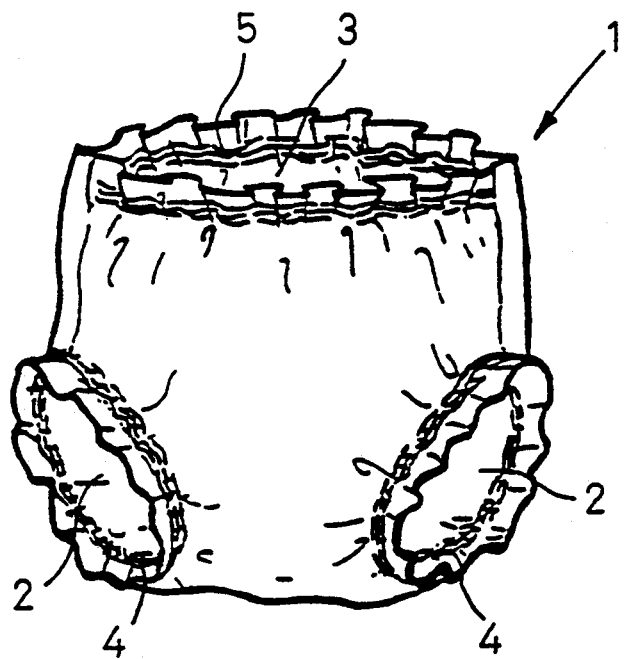
FIG. 1 is an isometric view showing a garment to be made by a method of the invention.

FIG. 1 is an isometric view exemplarily showing an garment made by a method according to the invention. The garment generally designated by 1 has leg-holes 2 and a waist (trunk)-hole 3 provided with elastic members 4, 5, respectively.

Figure 2:
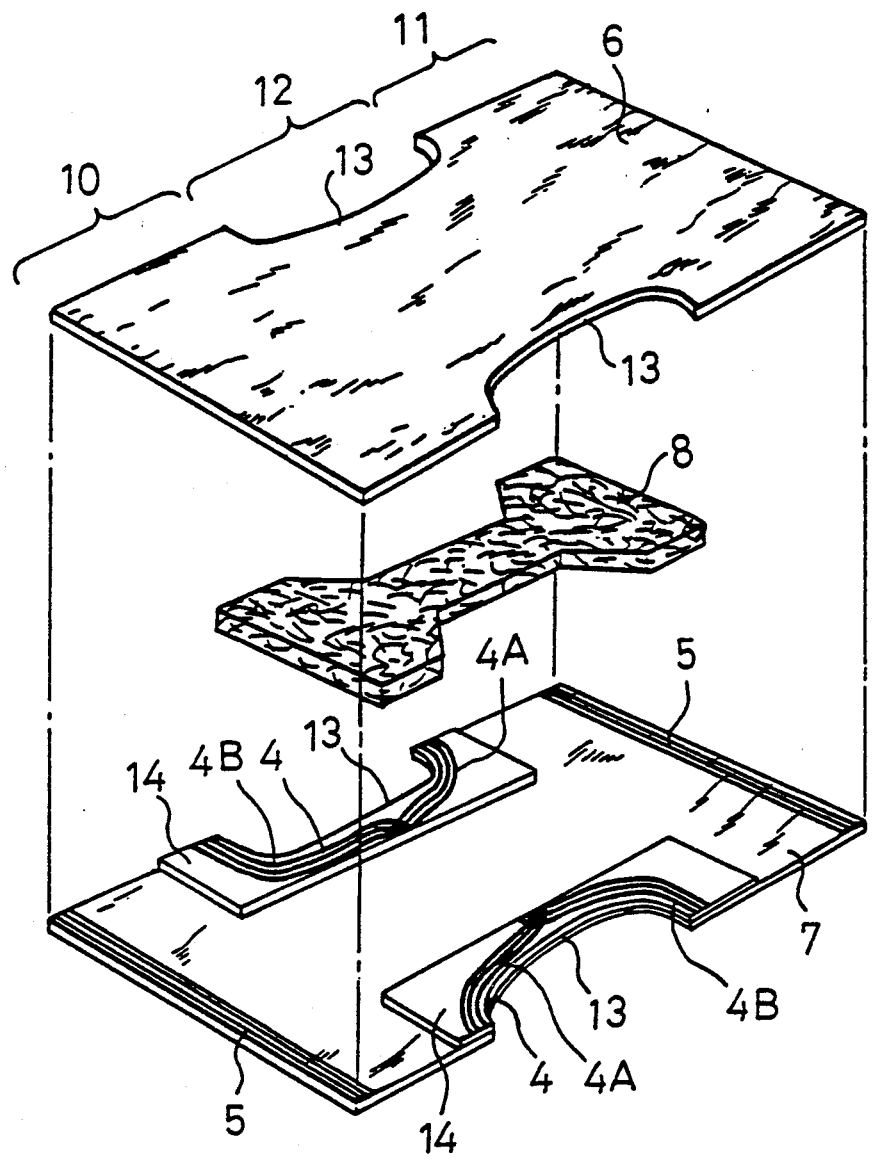
FIG. 2 is an exploded isometric view of the garment.

FIG. 2 is an exploded isometric view showing the garment 1. As shown, the garment 1 comprises a topsheet 6 made of nonwoven fabric which is stretchable both in length and breadth and liquid-permeable, a backsheet 7 made of nonwoven fabric which is stretchable both in length and breadth but liquid-permeable, a mat- or sheet-like liquid absorbent core 8 primarily made of fluffy pulp, and the elastic members 4, 5 provided around the leg-holes and waist-hole, respectively. A crotch zone 12 extending between front and rear sections 10, 11 of the top- and backsheets 6, 7 is formed along opposite side edges thereof with identical notches 13 defining the leg-holes 2. While it is not shown, the backsheet 7 may also comprise nonwoven fabric being stretchable both in length and breadth and liquid-permeable but additionally provided with plastic film intermittently bonded with adhesive onto an inner surface thereof, the plastic film also being stretchable both in length and breadth but liquid-impermeable. With such alternative arrangement, fluid excretions can be perfectly prevented from permeating the backsheet 7. In addition, a stretchability and, therefore, a stretch stress of the top-and backsheets 6, 7 as the main components of the garment 1 will be improved and thereby a fitness of the garment 1 onto the wearer's body will be further improved if the film is intermittently bonded with adhesive at least along the outer periphery onto the topsheet 6.

The elastic members 4 provided around the respective leg-holes are attached to the backsheet 7 on a top surface thereof along the opposite notches 13 with interposition of relatively thin base strips 14 (or strips 17' as will be described later) which are stretchable both in length and breadth, each comprising hydrophobic film or water-repellent nonwoven fabric or plastic film. The elastic member 4 comprises elastic sub-members 4A, 4b crossing each other at a longitudinal center of the associated one of the notches 13 and each of the elastic sub-members 4A, 4B comprises a plurality of thread-like elements made of natural or synthetic rubber. The elastic member 5 also comprises a plurality of thread-like elements and attached onto the backsheet 7 around the waist-hole.

Figure 3:
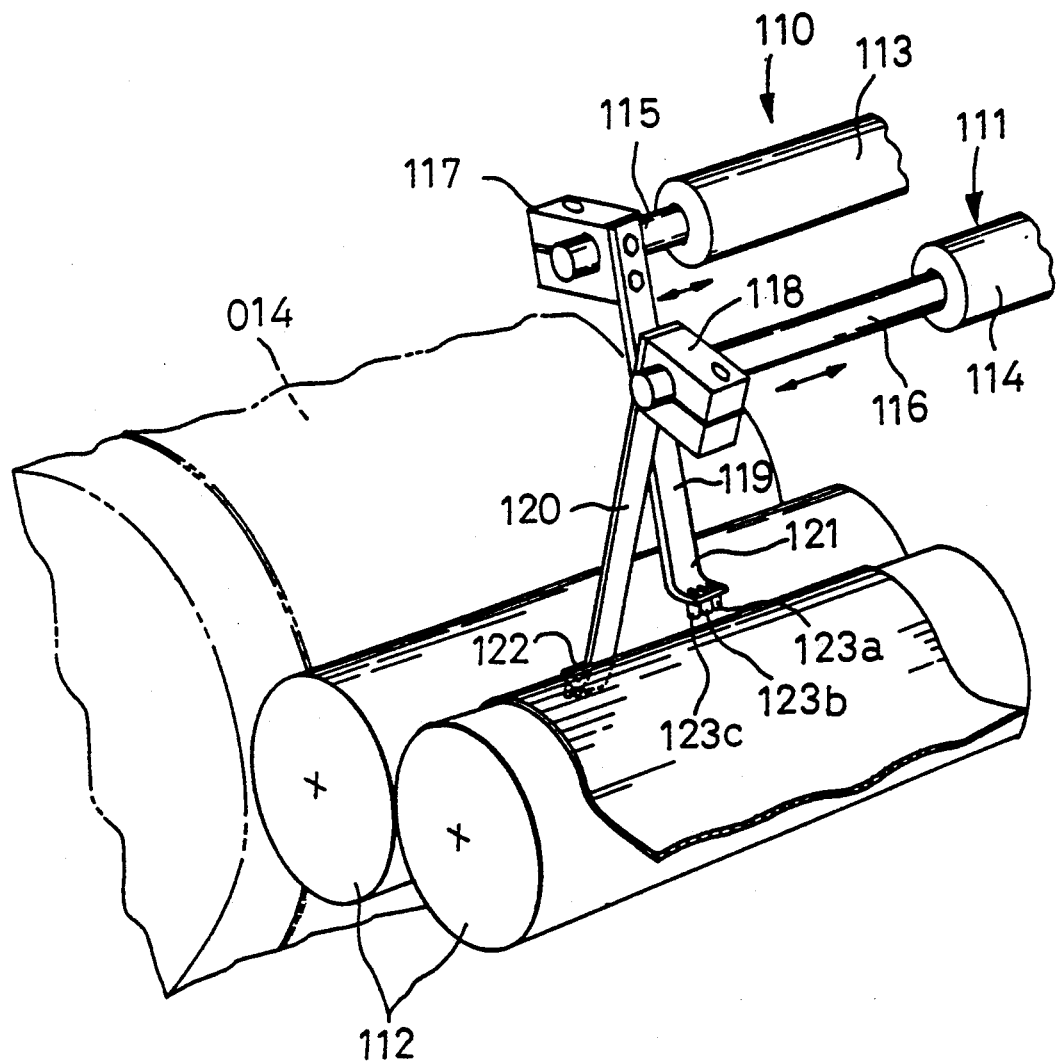
FIG. 3 is a schematic isometric view of traverse a means used to attach first and second continuous elastic members to a first web.
Figure 4:
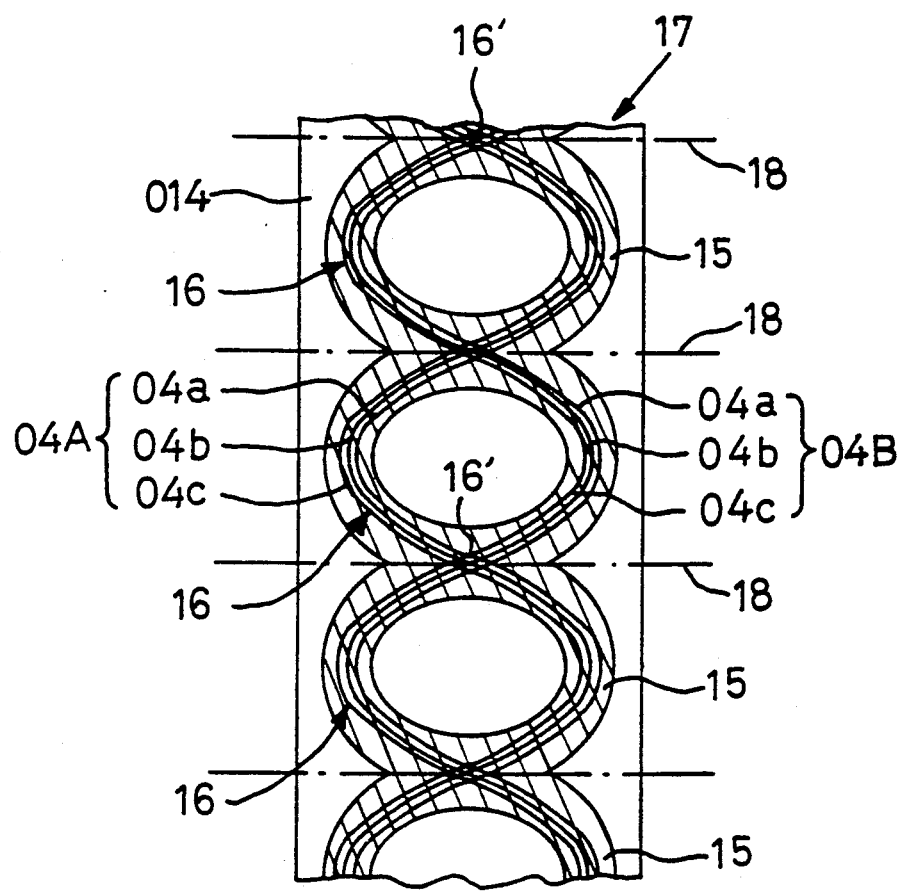
FIG. 4 is a plan view of a base web comprising the first web on which the first and second continuous elastic members have been attached by the traverse means.

FIG. 3 is an isometric view schematically showing a pair of traverse means 110, 111 used to attach first and second continuous elastic members from which the individual elastic sub-members are defined, respectively, onto a first web 014 from which individual base strips are defined in the manner as has previously been mentioned. FIG. 4 is a plan view showing a state in which first and second continuous elastic members 04A, 04B have been attached onto the first web 014. Such method for attachment is well know except for use of the traverse means and can be implemented using the conventional equipment for making disposable diapers, for example, as disclosed in EP 0405575 in the name of the applicant of the present application.

Referring to FIG. 3, a pair of taverse means 110, 111 comprise cylindrical supports 113, 114 extending adjacent and in parallel to a pair of squeezing rollers 112, slidable rods 115, 116 inserted into the respective cylindrical supports, and guide rods 119, 120 depending from respective support blocks 117, 118 secured to forward ends of the respective slidable rods. The guide rods 119, 120 are respectively provided at their crooked ends with small cylindrical guides 123a, 123b, 123c. These guides 123a, 123b, 123c are so arranged to be spaced one from another transversely of a first web 014. The crooked ends 121, 122 are closely adjacent to peripheral surfaces of the associated squeezing rollers 112. The slidable rods 115, 116 are under control of respective traverse cam mechanisms (not shown) operatively associated with base ends of these slidable rods.

Referring to FIG. 4, the first web 014 is coated with adhesive along its longitudinally extending central area as the first web 014 is moved at a given velocity longitudinally thereof so that elliptical adhesive zones 15 being continuous longitudinally thereof may be formed.

Meanwhile, thread-like elements 04a, 04b, 04c constituting first and second continuous elastic members 04A, 04B are inserted, while keeping them elongated at a given percentage, into the guides 123a, 123b, 123c of said traverse means 110, 111, respectively. Simultaneously, the guide rods 119, 120 are transversely reciprocated at a given velocity across the first web 014 so that the thread-like elements 04a, 04b, 04c forming the first and second continuous elastic members 04A, 04B, respectively, describe curves like sine curves on the respective adhesive zones 15. More specifically, the thread-like elements are guided so that summits as well as troughs of the respective curves described by the first and second continuous elastic members 04A, 04B are symmetrically opposed to each other and cross at their ends so as to form annular elastic areas 16 which are, in turn, forcibly bonded by the squeezing rollers 112 onto the respective adhesive zones 15 to form a continuous base web 17.

Figure 5:
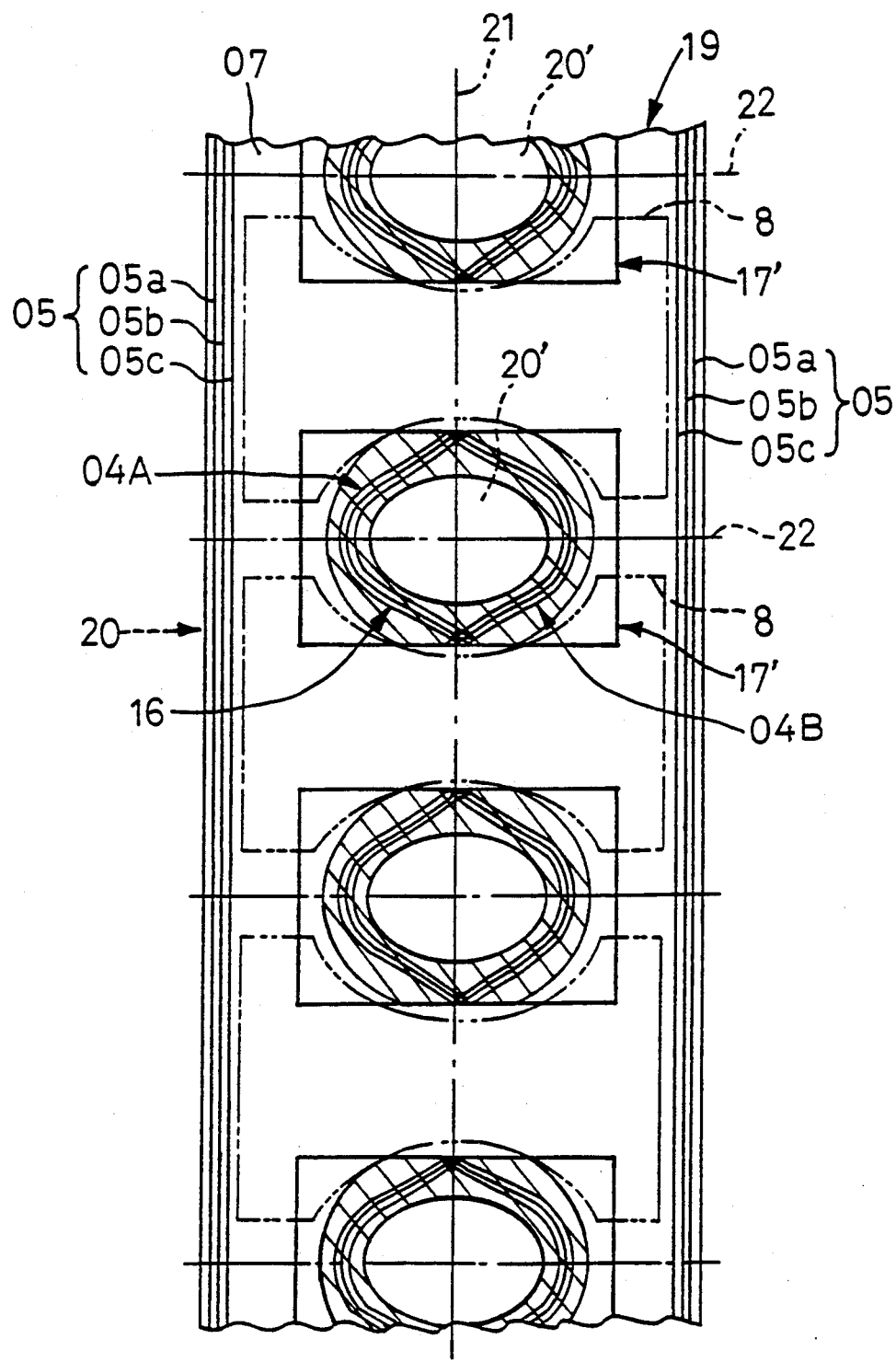
FIG. 5 is a plan view of an assembly comprising a second web, strips severed from the base web and intermittently bonded onto the second web so as to form a first composite web, and a core and a waist-hole elastic member attached on a top surface of the first composite web.
Figure 6:
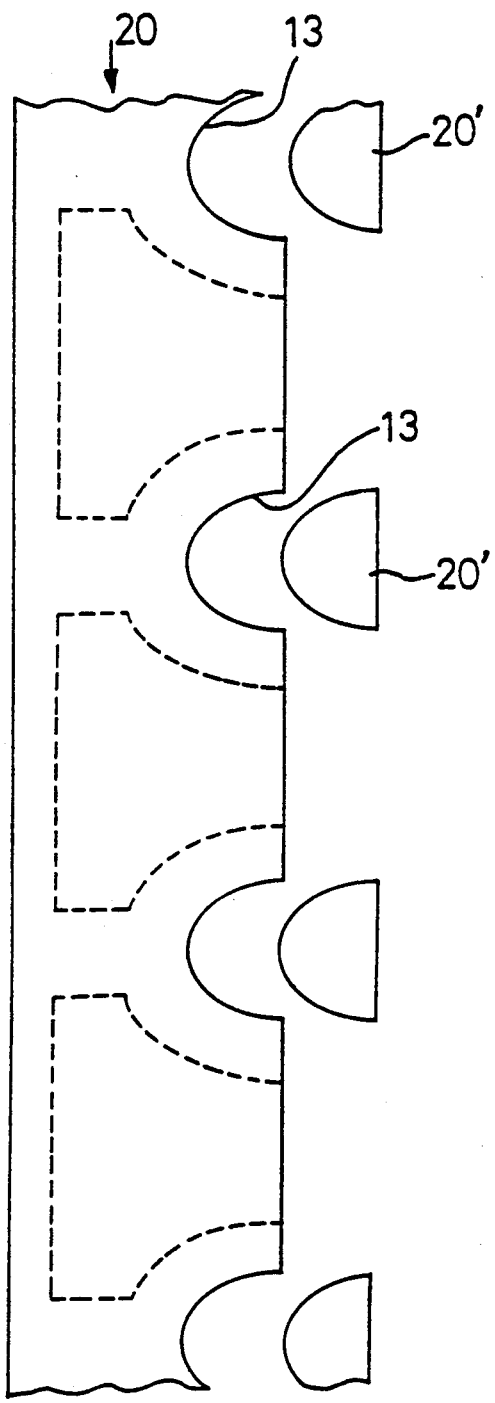
FIG. 6 is a plan view of an assembly comprising the first composite web, and a third web bonded onto the first composite web so as to form a second composite web, wherein disired portions of the second composite web have been cut away to form notches for respective leg-holes.
Figure 7:
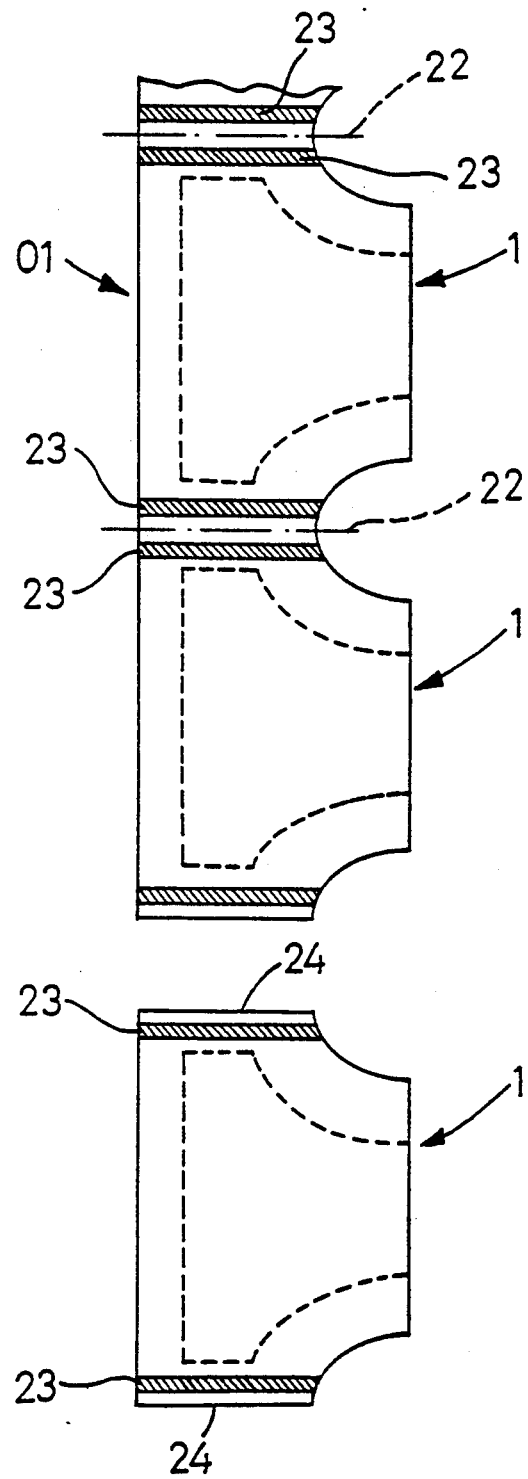
FIG. 7 is a plan view showing a state in which the second composite web has been provided at desired locations with seal lines to define individual garments and one of these individual garments has been severed from such second composite web.

FIG. 5 is a plan view showing a first composite web 19 comprising a second web 07 as the starting material of the backsheet 7 provided with the strips 17' which have obtained by severing the base web 17 and intermittently bonded with adhesive onto the second web 07. Operation of such cutting and bonding may be achieved, for example, by using the apparatus disclosed by the inventors in EP 0304044. FIG. 6 is a plan view showing a second composite web 20 partially cut away to form the notches 13 around the respective leg-holes. FIG. 7 is a plan view showing continuous garments 01 provided at given locations with seal lines 23 so as to define the individual garment 1.

Referring to FIG. 5, the base web 17 is severed along respective lines 18 transversely extending through crossings 16' at which the first and second continuous elastic members 04A, 04B cross each other to define the individual annular elastic areas 16 as shown in FIG. 4 and respective severed strips 17' are intermittently bonded with adhesive onto a second web 07 being moved, along its longitudinally extending central area. Simultaneously, thread-like elements 05a, 05b, 05c constituting together a waist-hole elastic member 05 are longitudinally bonded with adhesive onto opposite side edges of the second web 07 to form a first composite web 19.

Said core 8 which has previously been formed in a sandglass-shape is located between each pair of the adjacent annular elastic areas 16 and then a third web (not shown) as the starting material of said topsheet 6 is bonded with adhesive onto a top surface of the first composite web 19 to form a second composite web 20.

The second composite web 20 is transversely folded in two along its longitudinally extending center line 21.

Referring to FIG. 6, portions 20' of the second composite web 20 surrounded by respective said annular elastic areas 16 of FIG. 5 are cut away to form the notches 13 for the leg-holes.

Referring to FIG. 7, the composite web 20 is provided with a pair of transverse heat or sonic seal lines 23 extending on both sides of a line 22 (FIG. 5) dividing each the annular elastic area 16 in two longitudinally of the second composite web 20, thereby defining the 5 individual garment 1 and thus forming the continuous garments 01.

The individual garment 1 is severed off along the lines 22 away from the continuous garments 01 so that a pair of seal lines 23 may be left on each individual garment 1 so as to define opposite side edges 24 of this garment 1. Thus, the individual garment 1 as shown in FIG. 1 is obtained.

Formation of the notches 13 in the second composite web 20, i.e., cutting away of the portions 20' may be performed before or after folding of the second composite web 20, or after formation of the seal lines 23. In case of the garment of waist-hole open type, the seal lines 23 may be replaced by a tape fastener attached to a rear section of the garment on opposite sides thereof. For the garment requiring none of the core 8, it is obvious that the core 8 is not located on the first composite web 19.

While the invention has been described and illustrated as there are provided on said first web 014 the adhesive zones 15 for attachment of the first and second continuous elastic members 04A, 04B onto the first web 014, it is also possible to apply coating of adhesive directly on these elastic members. Though not shown, the guide rods 119, 120 may be provided at their lower ends with adhesive applicator means including the guides 123a, 123b, 123c and adhesive may be supplied from separately provided adhesive supply source via a flexible hose under a given pressure to the adhesive applicator means so as to be applied onto the thread-like elements constituting the respective continuous elastic members 04A, 04B longitudinally thereof. In this case, the applicator means (nozzle) disclosed by the applicant of the present application in U.S. Pat. Nos. 4,626,305 and 4,687,477 may be used as the applicator means.

According to the invention, the first and second continuous elastic members 04A, 04B are bonded with adhesive onto the first web 014 as the elastic members are curved by the traverse means 110, 111 substantially in sine curves, respectively as has already been mentioned. Therefore, the elastic members 04A, 04B preferably comprise the thread-like elements 04a, 04b, 04c. If these elastic members are relatively wide, these elastic members could not be properly bonded onto the continuous web and easily peel off from the web during operation of bonding since they should be twisted so far as the method of the invention is employed. The first and second continuous elastic members 04A, 04B may have circular (inclusive of elliptical), square or other indeterminate cross-section but it will be undesirable that a ratio of the maximum cross-sectional dimension to the minimum cross-sectional dimension is excessively large.

Attachment of the waist-hole elastic member 05 to the first composite web 19 may be achieved by using the conventional equipment and method for making disposable diapers. This elastic member 05 may also comprise a single tape-like member instead of the above-mentioned plural thread-like elements.

Unlike the method of prior art, the method of the invention allows the elastic members to be efficiently provided around the leg-holes without any useless portion of the elastic members connected between the both leg-holes. Additionally, the method of the invention provides the garments which are reinforced in proximity of the leg-holes and can effectively prevent leak of fluid excretions from occurring around the leg-holes.

What is claimed is:

1. A method for attachment of elastic members around leg-holes of a disposable garment, the method comprising steps of:
   a) forming a base web by continuosly feeding and bonding with adhesive first and second continuous elastic members, while keeping them stretched, onto a top surface of a first web, which is being moved, so that the elastic members describe undulating curves with summits as well as troughs of the respective curves being symmetrically opposed to each other and cross each other at their ends so as to form annular elastic areas;
   b) forming a first composite web by severing the base web along respective lines transversely extending through crossings at which the first and second continuous elastic members cross each other and intermittently bonding respective severed strips with adhesive onto a second web, which is being moved, along its longitudinally extending central area;
   c) forming a second composite web by bonding a third web, which is being moved, with adhesive onto a top surface of the first composite web;
   d) forming continuous garments by cutting off portions of the second composite web surrounded by the respective annular elastic areas to form notches for the leg-holes; and
   e) obtaining individual garments by severing the continuous garments along lines each dividing the associated one of the annular elastic areas in two longitudinally of the second composite web.

2. A method for attachment of elastic members around leg-holes of disposable garment, the method comprising steps of:
   a) forming a base web by continuously feeding and bonding with adhesive first and second continuous elastic members, while keeping them stretched, onto a top surface of a first web, which is being moved, so that the elastic members describe undulating curves with summits as well as troughs of the respective curves being symmetrically opposed to each other and cross each other at their ends so as to form annular elastic areas;
   b) forming a first composite web by severing the base web along respective lines transversely extending through crossings at which the first and second continuous elastic members cross each other and intermittently bonding respective severed strips with adhesive onto a second web, which is being moved, along its longitudinally extending central area;
   c) forming a second composite web by bonding a third web, which is being moved, with adhesive onto a top surface of the first composite web;
   d) folding the second composite web along its longitudinally extending center line which divides the second composite web in two transversely thereof;
   e) forming notches for respective leg-holes by cutting off portions of the second composite web surrounded by the respective annular elastic areas before or after said step (d);
   f) forming continuous garments by providing the second composite web with seal lines along lines dividing the respective annular elastic areas in two and thereby defining the individual garments; and g) severing off the individual garments from the continuous garments, simultaneously with or after said step (f), so as to leave the seal lines and thereby to define side edges of the respective individual garments.

3. A method according to claim 1 wherein said undulating curves are in the form of sine waves.

4. A method according to claim 2 wherein said undulating curves are in the form of sine waves.

* * * * *